(12) United States Patent
Weiss (10) Patent No.: US 6,394,950 B1
(45) Date of Patent: May 28, 2002

(54) SURGICAL INSTRUMENT

(76) Inventor: Sol Weiss, 7012 Reseda Blvd. Suite A, Reseda, CA (US) 91335

( * ) Notice: Subject to any disclaimer, the term of this patent is extended or adjusted under 35 U.S.C. 154(b) by 0 days.

(21) Appl. No.: 09/978,604

(22) Filed: Oct. 15, 2001

Related U.S. Application Data (60) Provisional application No. 60/241,067, filed on Oct. 17, 2000, and provisional application No. 60/286,188, filed on Apr. 24, 2001.

(51) Int. Cl.[7] ................................................. A61B 1/32
(52) U.S. Cl. ....................... 600/205; 600/222; 600/223; 600/210; 600/220
(58) Field of Search ................................ 600/201, 205, 600/214, 219, 220, 221, 222, 223, 224, 245, 246, 210

(56) References Cited

U.S. PATENT DOCUMENTS

| | | | | |
|---|---|---|---|---|
| 559,122 A | * | 4/1896 | Daily | |
| 688,935 A | * | 12/1901 | Crane | |
| 872,344 A | * | 12/1907 | Griswold | |
| 2,483,233 A | * | 9/1949 | Price et al. | |
| 3,040,738 A | * | 6/1962 | Moore | |
| 3,565,061 A | * | 2/1971 | Reynolds | |
| 3,815,585 A | * | 6/1974 | Fiore | |
| 4,884,559 A | * | 12/1989 | Collins | |
| 5,499,964 A | * | 3/1996 | Beck et al. | 600/220 |
| 5,868,668 A | * | 2/1999 | Weiss | 600/224 |
| 6,048,308 A | * | 4/2000 | Strong | 600/205 |

* cited by examiner

*Primary Examiner*—Jeffrey A. Smith
(74) *Attorney, Agent, or Firm*—Gerald L. Price (57) ABSTRACT

A surgical instrument having an upper and a lower blade member, each of the members having a main generally elongated blade portion, each of the members having spaced upstanding lateral sidewalls, the upper blade member being vertically, movable with respect to the lower blade member to selectively open and close the spacing between the blade members.

A light cone may be provided in the upper blade member for connection of an illuminating device for providing light to the surgeon's work area. A port may also be provided in the upper blade member for connecting a suction tube thereto for removing fluids and the like during use of the instrument.

19 Claims, 6 Drawing Sheets

SURGICAL INSTRUMENT

CROSS-REFERENCE TO RELATED APPLICATIONS

This application contains subject matter of my provisional application Ser. No. 60/241,067, filed Oct. 17, 2000, entitled Surgical Instrument, and in my provisional application Ser. No. 60/286,188, filed Apr. 24, 2001, entitled Light Cone.

BACKGROUND OF THE INVENTION

1. Field of the Invention

The invention relates to surgical instruments, and, more particularly, to diagnostic and surgical instruments for use in abdominal, thoracic, vaginal, anal or other surgical procedures that may also include endoscopies.

2. General Background and State of the Art

Certain surgical and diagnostic devices are known for examining vaginal and other cavities. For example, women of a certain age should have a diagnostic pap smear annually. Certain prior art devices, known as speculums, are used which consist of a pair of wide or broad blades.

Also, when such instruments are used in examining a body cavity, such as the vagina, a second instrument is inserted into the vagina through the speculum. Such an instrument is called a lateral vaginal retractor and is used to retract the vaginal sidewalls which normally obstruct the doctor's view into the patient's cervix. During a surgical procedure, the surgeon needs to insert a clamp, a source of lighting, a suctioning catheter, and irrigation tube through the speculum, thus further obstructing the surgeon's view of the cervix which might interfere with the surgical procedure being performed.

In my U.S. Pat. No. 5,868,668, I disclose a surgical and diagnostic instrument which eliminates the need for an external lateral vaginal retractor during vaginal surgery. The instrument is anatomically designed with a narrow oval shape in its closed position to allow it to be inserted comfortably into the patient's vagina without the discomfort generally associated with a conventional speculum. It also allows the introduction of other instruments such as a light, an irrigation tube, etc. without obstructing the surgeon's view.

In my pending application Ser. No. 09/578,016, filed May 24, 2000 (pending), I disclose an improvement of the surgical device in my patent wherein the upper blade is U-shaped in cross-section having lateral blades for improved visualization.

In my provisional application Ser. No. 60/241,067, filed Oct. 17, 2000, entitled Surgical Instrument, I disclose a vaginal speculum having a first vertical blade which is hinged and extends outwardly and upward with two lateral blades attached. The second blade contains the tracks for the first blades for adjustable hinging and two mounted rectangular lateral angled braces that permit both lateral blades of the first component to pivot outwardly and increase the tension of the outward portions of the lateral blade. This provides a greater resistance against the tissues that might otherwise bend the distal portions of the blades inwardly thereby obscuring the view of the operator. Also, the lateral blades prevent vaginal and other membranes from cascading inwardly and obstructing the view. Thus, the instruments and operative procedures can be more easily and efficaciously managed through the aperture between the spread-apart four blades.

Thus, I disclose an upper blade having two spaced side lateral blades. The lower blade has two side lateral blades. Although such a speculum has obvious advantages, I find that there is a need for having these upper side lateral blades integral with the upper blade rather than hinged thereto as in my provisional application, and, as will be discussed hereinbelow, have multiple blades in vertical and lateral positions.

In my provisional application Ser. No. 60/286,188, entitled Light Cone and filed Apr. 24, 2001, I disclose a light cone for use with a surgical instrument, such as the speculum in my U.S. Pat. No. 5,868,668 and in my pending application.

There is thus a need for a surgical instrument, such as a speculum, to have multiple blades in vertical and lateral positions along with provisions for a light cone.

SUMMARY OF THE INVENTION

It is an object of this invention to provide a multi-bladed, vaginal diagnostic and surgical instrument which is quickly and easily activated to expand the blades with slight rotation movement and with little discomfort to the patient having multiple blades in vertical and lateral positions.

It is still further an object of this invention to provide such an instrument having a portable light cone for illuminating the surgeon's working area without interfering with the surgeon's view through the instrument, avoids contamination with the surgical procedure and is away from the containment area and away from the bleeding area and is reusable.

It is another object of this invention to provide such a surgical instrument having a passageway for feeding a suction tube therethrough to suction out blood, smoke or tissue or the like during an invasive procedure without interfering with the surgeon's view through the instrument.

These and other objects are preferably accomplished by providing a surgical instrument for spreading apart openings of natural orifices or surgically made openings to perform procedures on internal structures and/or organs of a patient. The instrument includes a main body portion having multiple blades in vertical and lateral positions that open to spread apart the area being examined so that a surgical tool can be inserted therein.

The instrument has a light cone associated therewith for illuminating the surgeon's work area and a passageway through which a tube may be fed to suction out smoke, blood gases, or tissue or the like.

DETAILED DESCRIPTION OF THE PREFERRED EMBODIMENTS

Figure 1:
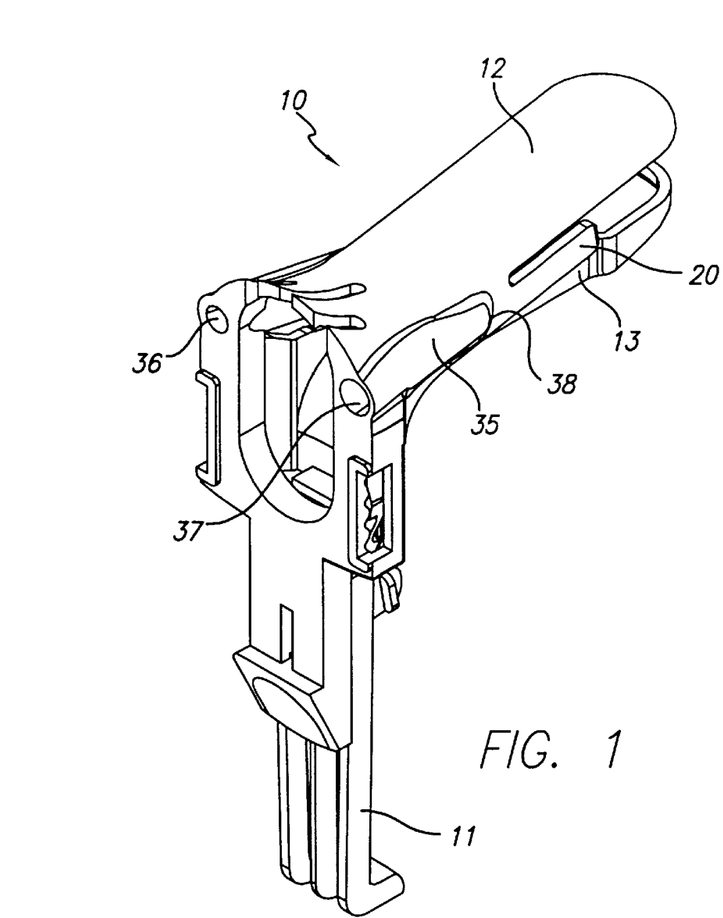
FIG. 1 is a rear perspective view of an assembled surgical instrument in accordance with the teachings of the invention.
Figure 2:
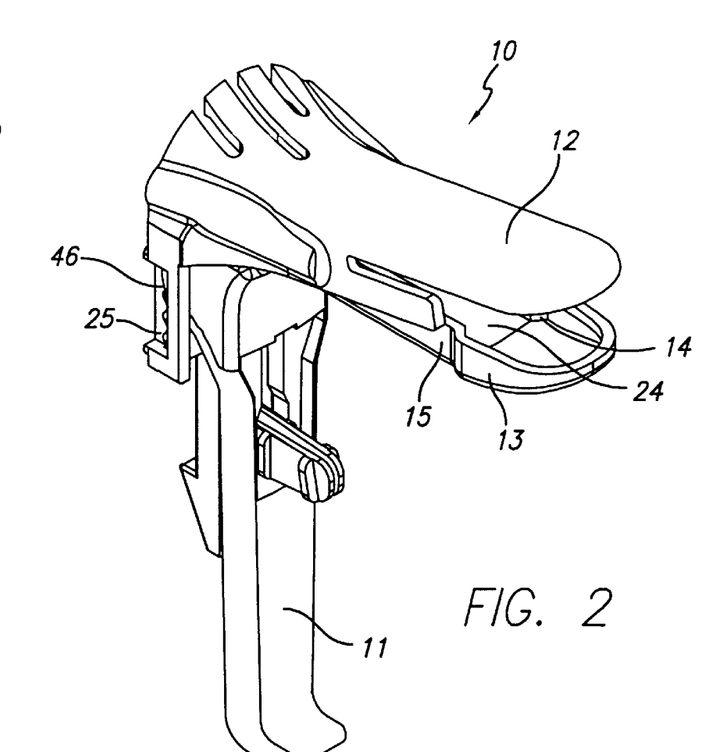
FIG. 2 is a front perspective view of the surgical instrument of FIG. 1.

Referring now to FIG. 1, a surgical instrument 10 is shown having a handle 11. A pair of upper and lower blades 12, 13, respectively, are provided. Blade 13 is an integral part of handle 11 and, as seen in FIG. 2, has a generally flat or slightly concave in cross section interior surface 14 and a pair of spaced upstanding sidewalls 15, 16 forming lower vertical blade portions.

Figure 3:
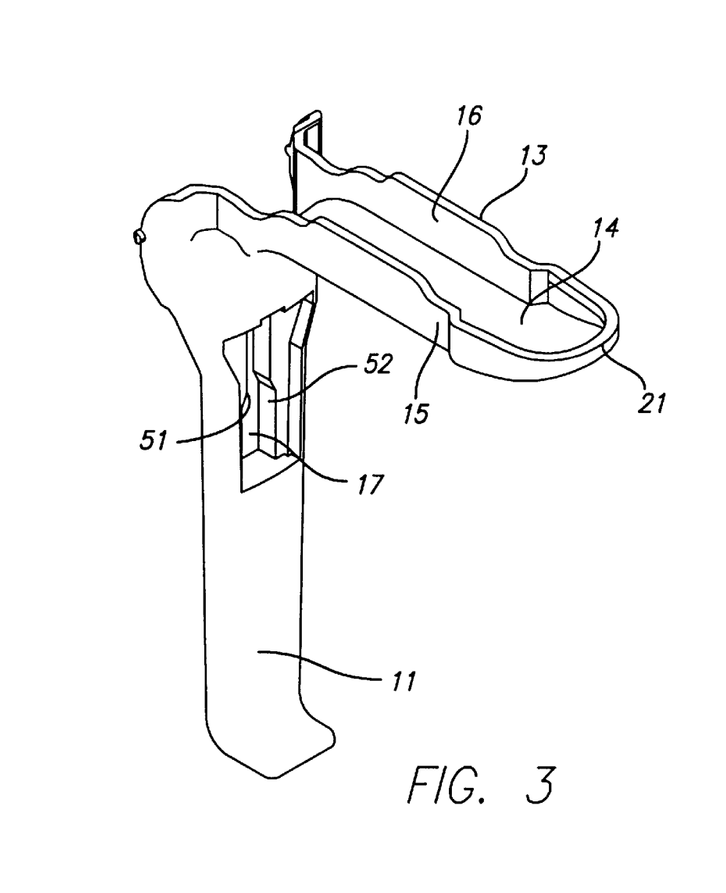
FIG. 3 is a front perspective view of the lower blade member alone of the surgical instrument of FIGS. 1 and 2.

As seen in FIG. 3, wherein handle 11 and blade 13 are shown removed from upper blade 12, an opening 17 is provided through handle 11. Opening 17 (see also FIG. 4) has a lower end portion 18 wider than upper portion 19.

Figure 4:
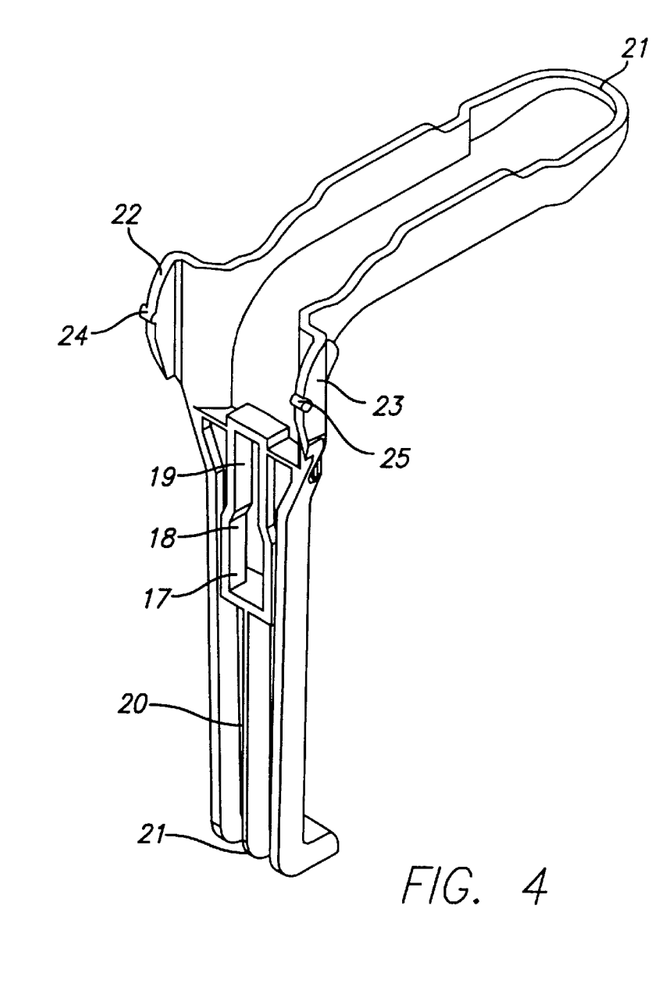
FIG. 4 is a rear perspective view of the lower blade member of FIG. 3.

A rib or flange 20 extends from opening 17 to the bottom terminal end 21 of handle 11. Also as seen in FIGS. 3 and 4, upstanding walls 15, 16 curve around and meet at front curved wall portion 21 integral therewith.

The rear end (opposite curved portion 21) of blade 13 above opening 17 has a pair of spaced outwardly extending curved flanges 22, 23 each having a nub (as nubs 24, 25, respectively) extending outwardly therefrom for reasons to be discussed.

Figure 5:
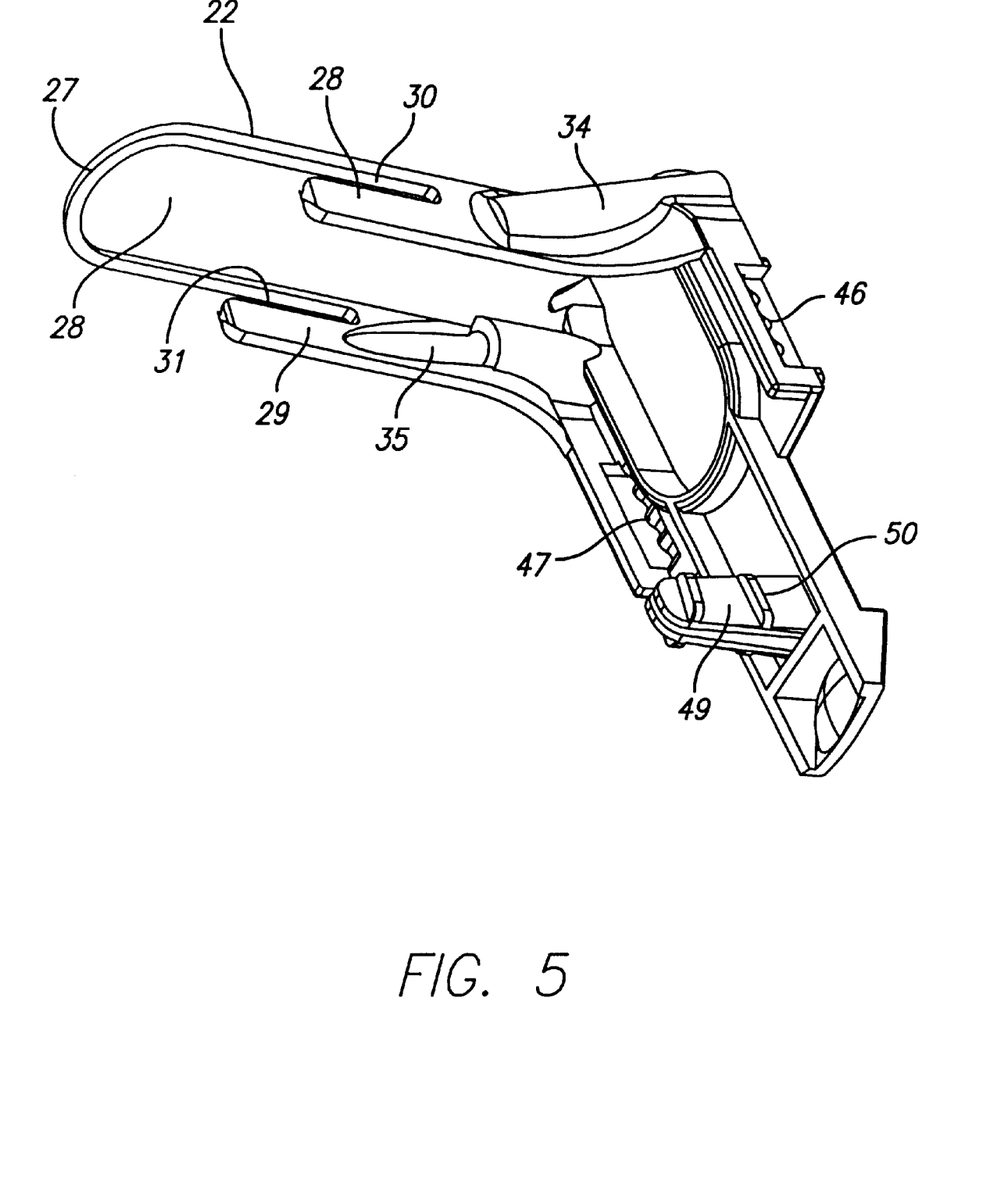
FIG. 5 is a front perspective view of the upper blade member alone of the surgical instrument of FIGS. 1 and 2.

The upper blade 12 is shown removed from lower blade 13 in FIG. 5. It can be seen that blade 12 has a generally flat or slightly concave in cross-section undersurface 26 and is curved at its front end 27. A pair of downwardly extending elongated flanges 28, 29, spaced from blade 12 forming slots 30, 31, respectively, are provided on each side of blade 12.

Figures 6, 7, 8:
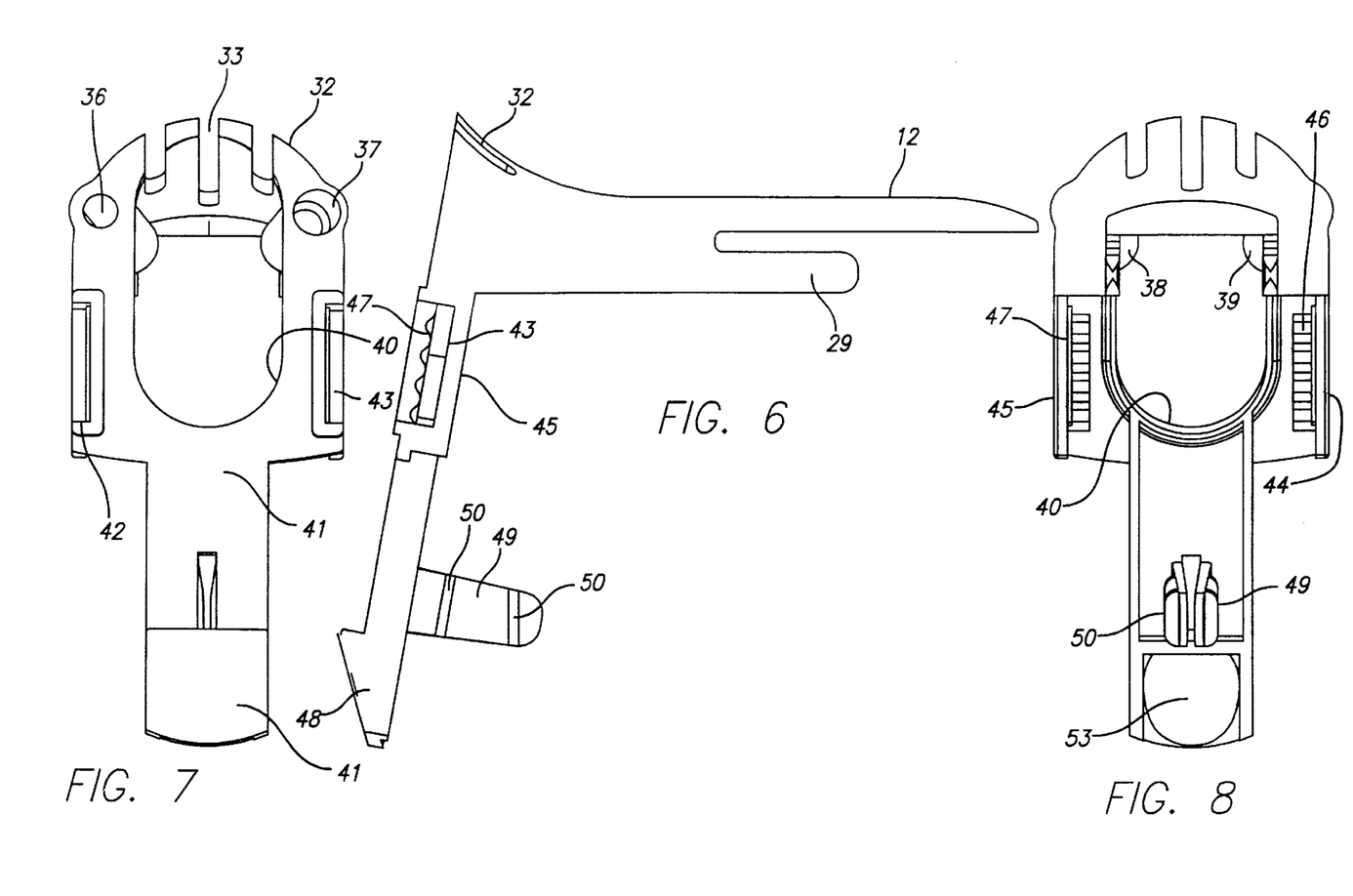
FIG. 6 is a side elevational view of the upper blade member of FIG. 5.
FIG. 7 is a rear elevational view of the upper blade member of FIG. 5.
FIG. 8 is a front elevational view of the upper blade member of FIG. 5.

As seen in FIG. 6, blade 12 curves rearwardly and upwardly forming an upper section 32 which may be slotted, as at spaced slots 33 (FIG. 7). Referring again to FIG. 5, a pair of ports 34, 35, respectively, are provided aligned with each flange 28, 29, respectively. These ports having openings leading therein (openings 36, 37 for ports 34, 35, respectively, shown in FIG. 7) for use during an operation as will be discussed.

Ports 34, 35 are generally similar (see also FIG. 1) each having an opening, such as opening 37, leading into a closed chamber aligned with its respective flange, such as flange 29. However, port 35 is closed at its forward end 38, for reasons to be discussed, whereas port 34 is open at open end 39 (FIG. 8). Both parts 34, 35 may be tapered from its respective opening 36, 37 to its forward end.

As seen in FIG. 7, upper blade portion 12 has a U-shaped cut out area 40 below section 32 with an extension portion 41 extending downwardly from area 40. A pair of elongated openings or slots 42, 43 are provided in sidewalls 44, 45 respectively (see FIGS. 6 and 8). As seen in FIG. 6, each opening 42, 43 has a plurality of grooves 46, 47 (FIGS. 5, 6 and 8) extending along one side of each opening 42, 43 for reasons to be discussed.

Extension portion 41 terminates at its lowermost end in a V-shaped wedge portion 48. Also, a latch member 49 (see also FIG. 8) extends outwardly from extension portion 41 above wedge portion 48 having a plurality of spaced ribs 50 (see FIG. 5) thereon adapted to engage and ratchet with the sidewalls 51, 52 (FIG. 3) of opening 17 as will be discussed thereby providing ratchet means for the instrument 10. As seen in FIG. 8, wedge portion 48 has a concave thumb rest area 53 for reasons to be discussed.

Figure 9:
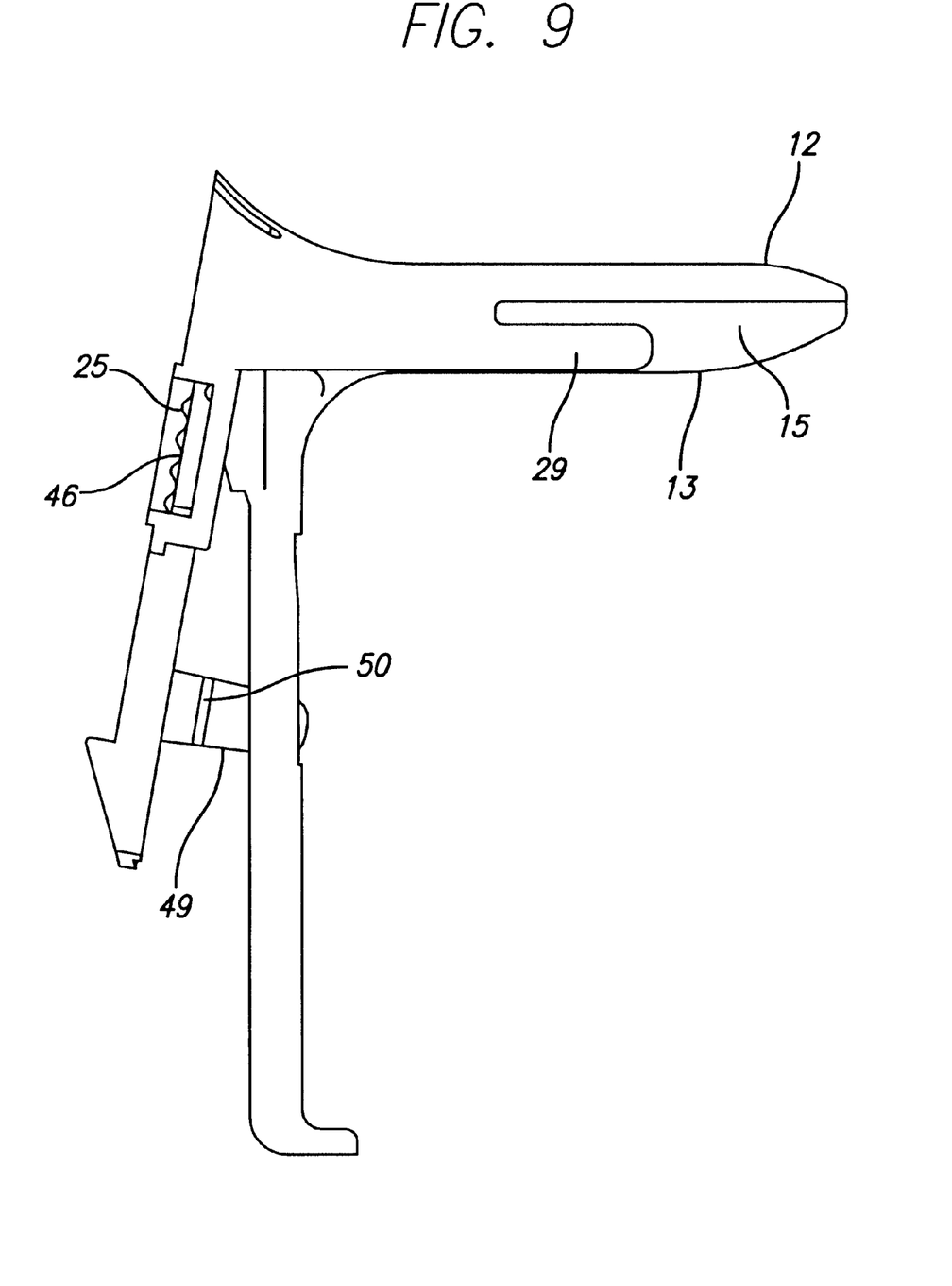
FIG. 9 is a side elevational view of the assembled upper and lower blade members of the surgical instrument of FIGS. 1 and 2.

The assembly of the part shown in FIGS. 3 and 4 to the part shown in FIGS. 5 to 8 is shown in FIGS. 1 and 2. The latch member 49 is extended into opening 17 (FIG. 2). As seen in FIG. 9, when, one of the ribs 50 of latch member 49 engages and is stopped by its engagement with sidewall 51 (FIG. 3). Nubs 24, 25 (FIG. 4) engage one of the grooves in ratchets 46, 47 (FIG. 5), e.g., the uppermost groove in FIG. 9, thus allowing flanges 28, 29 to extend on the outside of each sidewall 15, 16 when the upper and lower blades 12, 13 are in the FIG. 9 closed position.

Pushing up on the extension portion 41 via thumb rest area 55 moves extension portion 49 upwardly within opening 17 to allow ribs 50 to engage the sidewalls in the upper narrower portion 19 of opening 17 as shown in FIGS. 1 and 2 thus opening or separating blades 12, 13. The upper end of opening 17 acts as a stop and nubs 24, 25 move downwardly along the grooves of ratchets 46, 47 (see nub 25 and ratchet 46 in FIG. 2) providing ratchet means for the instrument 10.

It can be seen that there is disclosed an improved Surgical Instrument over that disclosed in my U.S. Pat. No. 5,868, 668, the teachings of which are incorporated herein by reference. In this patent, I disclose how such a surgical instrument is used for spreading apart openings of natural orifices or surgically made openings to perform procedures on internal structures and/or organs of a patient. The instrument includes a plurality of blades that open to spread apart the area being examined so that a surgical tool can be inserted therein as discussed in my patent. The wide opening 40 allows the instrument to be eliminated from the area of view by allowing the surgical tool to pass therethrough while maintaining the spread-apart condition of the area being examined. The blades can then be restored to their closed position after the tool is withdrawn.

However, in the instant invention, the side blades are an integral part of the lower member and the upper member also has side or lateral blades.

Port 35 is a light chamber in the form of a curved solid plastic cone tapered at its forward end to transmit light.

Figures 10, 11, 12, 13, 14, 15, 16:
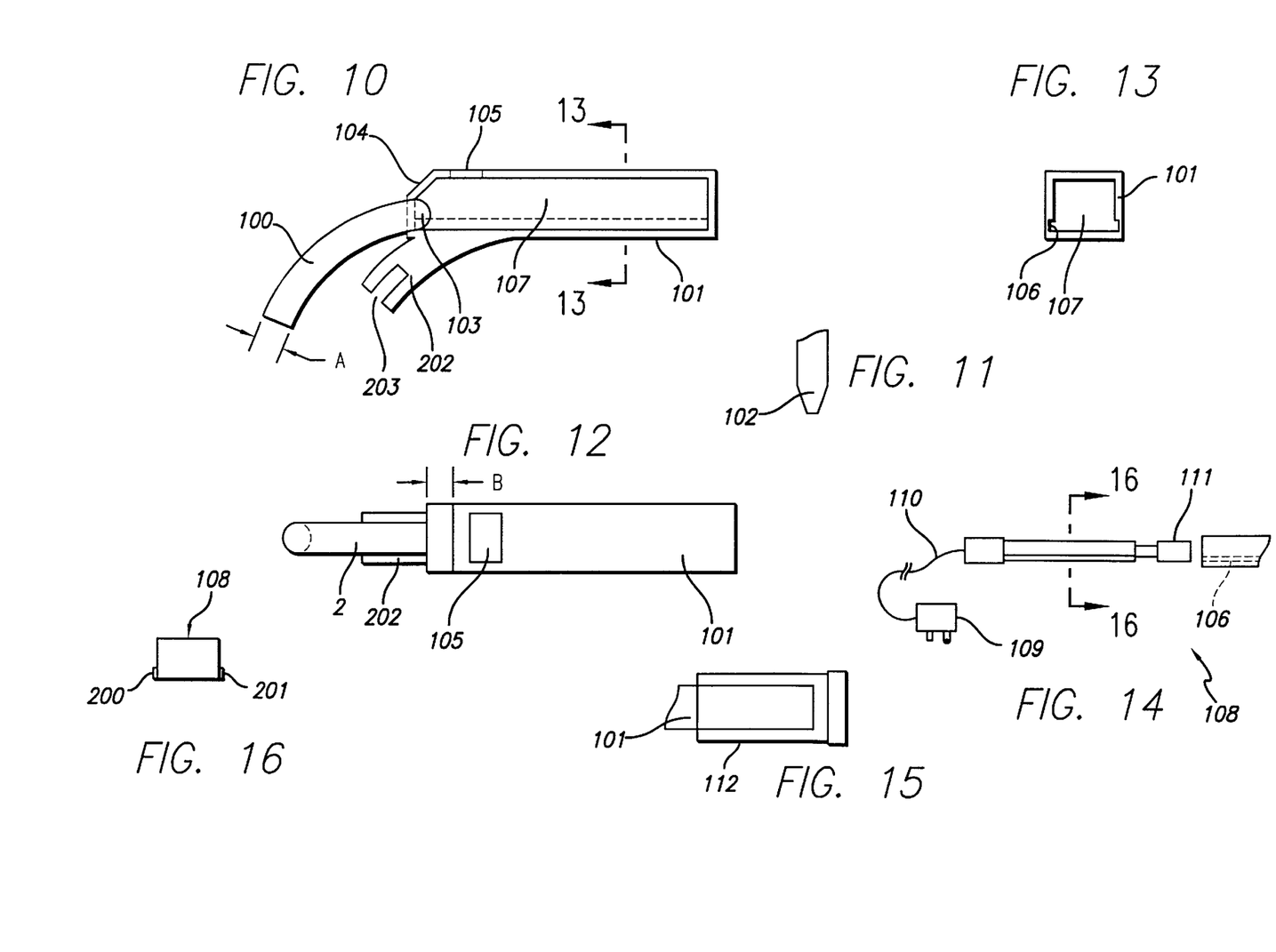
FIG. 10 is an elevational view of a light transmitting device adapted to be used with the surgical instrument of FIGS. 1 to 9.
FIG. 11 is a detailed view of a light carrying cone of FIG. 10.
FIG. 12 is a top plan view of the device of FIG. 10.
FIG. 13 is a view taken along lines 13—13 of FIG. 10.
FIG. 14 is an elevational view of a prior art illuminating device used with the device of FIG. 10.
FIG. 15 is an elevational view of a resilient sleeve adapted to be used with the device of FIG. 10.
FIG. 16 is a view, taken along lines 16—16 of FIG. 14.

As seen in FIG. 10, a portable light carrying cone 100 is shown having a base or connector body 101, which may be of clear plastic, directing light from an illuminator or other light sources. The cone 100 shown here is solid and has a tapered distal portion 102 (FIG. 11) and a bulb like proximal end 103 (FIG. 10), within the connector body 101. The tapered portion 102 of the cone 100 is used to fit snugly or tightly into the end 37 (FIG. 1) of cone 35 so that light can be transmitted. The bulb shaped proximal portion 103 (FIG. 10) acts as a magnifier to attract light rays concentrating them into the cone 100 for transmitting the light. The tapered portion 104 of the connector body 101 allows for non-cone absorbing light to be scattered into the area where the cone 100 and body 101 of the connector are directed.

FIGS. 10 and 12 show the window opening 105 in body 101 that allows for heat to be dissipated, and the tracks 106 at the bottom of the opening 107 stabilize the illuminator body 101 and center it so that the bulb of the lighting device, to be discussed, doesn't come in contact with the walls of the connector body 101.

FIG. 14 shows a conventional prior art illuminating device 108 having a transformer 109, an electrical cord 110, and a light source 111. Light source 111 is shown inserted into cone 100, the terminal or bulb end extending to bulb end 103 (FIG. 10). Any suitable illuminator may be used. For example, the vaginal illuminator system No. 78103 manufactured and sold by Welch Allyn of Skaneateles Falls, N.Y., may be used. The opening 107 and sidewalls (FIG. 13) of housing 101 accommodate the outer configuration of light source 111.

The angled tapered front portion 104 of the body 101 permits light to be dispersed to different areas that are targeted as well. The body 101 of the connector also has tracks or slots 106 (FIG. 13) to receive flanges 200, 201 (FIG. 16) on the outer body of the illuminator 111 and its bulb to allow for not stabilizing the light bulb thereof into the center of the cavity 107 of the body 101 so that is does not contact the walls (FIG. 13) of the connector body 101.

The posterior portion of the connector body 101 may have an elastic or rubber adapter 112 (FIG. 15) with a hollow tubular interior so that the end of the body 101 fits therein for attaching to different light illuminating devices which may be of different sizes.

The cone 100 and connector body 101 are portable, and they are not dependent on other devices or handles. They are not sacrificed with each procedure, as other equipment requires them to be.

The cone 100 and body 101 may be of a simplified plastic construction that allows for easy manufacturing as a two-part injection mold for plastic applications. This can also be made by metal molding or casting. The tapered tip 102 produces a tight connection with a circular opening, such as opening 37, in any instrument receptacle designed for this procedure.

Body 101 has an open area 105 of the connector body 101 near the cone projection that allows heat to escape caused by the bulb of illuminator 111.

Cone 100 has a curved cone projection 103 that may be solid plastic and provides the transmission of the light from the bulb of illuminator 111 or any other source to a specific area directed by the tip of the cone 100 out through end 38 which my be of clear plastic.

There thus is disclosed in FIGS. 10 to 16 a light connector possessing at its front portion a curved solid plastic cone tapered at its distal end for light transmission. The connector body unites with the cone having a bulb shaped proximal portion that allows for light to be collected and transmitted to the end of the curved cone. This allows light to be carried into difficult areas as well as directed to the front of medical devices through an aperture that permits the tapered cone to fit tightly. The connector body of this unit has a slot opening in the rear portion permitting the light bulb and the illuminator body to penetrate into the cavity of the connector body. The connector body has a tracking mechanism that keeps the illuminator and light bulb in a central position without touching the inner walls of the plastic housing of the connector body. The front portion of the connector body has a window opening that permits the escape of heat from the illuminator bulb.

Any suitable catheter tube can be inserted into opening 36 to suction fumes or fluids during any surgical procedure. Such a tube, such as ¼" tubing, can friction fit into opening 36.

The upstanding sidewalls 15, 16 of the lower blade member act as shields or protectors so, for example, vaginal membranes do not cascade into the device during a surgical procedure.

The slots 33 (FIG. 7) can be used to insert a tube for lighting, or a handle of a tenaculum or a suction tube. The lower blades 15, 16, along with the central cavity surrounded by blades 15, 16, keep blood or the like from a surgical procedure from dripping on equipment below. The upper portion can be removed from the lower portion of the instrument 10.

The improved surgical device disclosed herein has the following improvements over prior art devices:

1. Lateral Wall retraction with unobstructed view
2. Light Port
3. Suctioning Port
   (a) Fumes
   (b) Intrauterine Procedures
4. Tenaculum Port or Ports
5. Wide blades
6. Narrow blades
7. Diagnostic Applications
8. Surgical Applications
9. Disposable
10. Clear Plastic Any suitable dimensions may be used. The materials may be in the thickness range of 0.03 to 0.10 inches and the length of the lateral blades may be in the range of 2 to 6 inches. Plastic or metal can be used. The lateral blades may constitute a component (attached) to the top vertical blade as seen in FIG. 1. The lateral blades may constitute a component (attached) to the bottom vertical blade as seen in FIG. 1. If the top portion is removed from the bottom portion, an instrument is created having two lateral blades. If the top portion is attached, a four blade instrument is provided.

The vertical and lateral blades are conduits for the light transmission or the lateral blades may alone carry fiberoptic light and/or tube attachments for suctioning as discussed. As a consequence of this application, the thickening of the structure of the lateral blades may offer more strength in their capacity to retract tissue. Light transmissions for all or part of the blades may be part of the electromagnetic spectrum, i.e., ultraviolet and infrared for diagnostic and treatment purposes.

The proximal portion of the top, vertical blade contains three U-shaped openings 33. These openings or slots may be used for hooking instruments, light or suctioning tubes or any combination of these.

The tracks for lateral portions of the vertical blades avoids lateral movement. The lower anterior of the top vertical blade handle has a projection as a trigger for mating, releasing and contains a nubbing 24 and 25 for locking the vertical blade's position.

All four blades have a fixed position. The lateral or side blades may have a longitudinal curvature for strength. The bottom vertical side blades act as a recess for lateral blades with speculum. This recess formation allows for the collection of blood and/or tissues (a reservoir) from the surgery.

The bottom blade may have a mid and an outward angular brace that will force the lateral blades outward (2 to 15 degrees). These spread the lateral blades outward (laterally) with a force to avoid inward bending of their distal tips. The handles of both vertical blades may be darkened to allow for light transmission to the distal portions of the blades for lighting.

The wide web-like base between the lateral blades imparts greater strength to the lateral blades so as to resist inward bending of the blades. The vertical blades in the closed position are flushed and smooth for use. The tips of all blades may be smooth and rounded to avoid injury to the patient. All blades may be in varying sizes in length, width, etc. for pediatric and adult usage.

The lateral walls of the vertical blades have gates for holding instruments and ties as necessary while performing surgical procedures as discussed in my U.S. Pat. No. 5,868,668. Any suitable colors may be used. The bottom blade contains a center recess for holding instruments. The blades may be coated for use with lasers. Finally, special plastics may be used for re-useable instruments that can withstand sterilization.

While the specification describes particular embodiments of the present invention, those of ordinary skill can devise variations of the present invention without departing from the inventive concept.

I claim:

1. A surgical instrument for carrying out diagnostic and therapeutic procedures on the interior organs of the human body comprising:
    a first upper blade member having an elongated main blade portion;
    an integral handle portion extending downwardly generally normal to said main blade portion;
    a pair of integral spaced lateral side blades extending along opposite sides of said main blade portion and downwardly therefrom;
    a second lower blade member having an elongated main blade portion;
    an integral handle portion extending downwardly generally normal to said main blade portion of said lower blade member;
    a pair of integral spaced lateral side blades extending along opposite sides of said main blade portion of said lower blade member extending toward said side blades of said upper blade member when said upper blade member is assembled to said lower blade member; and
    said handle portion of said upper blade member being reciprocally mounted to the handle portion of said lower blade member, and ratchet means associated with said upper and lower blade members for ratcheting said handle portions to a plurality of positions therealong when said upper blade member handle portion is reciprocated along said lower blade member handle portion.

2. The instrument of claim 1 wherein said main blade portion of said upper blade member is slightly arcuate in cross section and curved at the forward end thereof.

3. The instrument of claim 1 wherein said main blade portion of said lower blade member is slightly arcuate in cross section and curved at the forward end thereof.

4. The instrument of claim 3 wherein said main blade portion of said lower blade member is upturned at the forward end thereof, said sidewalls of said lower blade member curving into said curved end thereof.

5. The instrument of claim 1 wherein said side blades of said upper blade member have a slot between said main blade portion of said upper blade member and said side blades of said upper blade member.

6. The instrument of claim 1 wherein said upper blade member has a generally U-shaped opening area rearwardly of said main blade portion extending downwardly therefrom to said handle portion of said upper blade member.

7. The instrument of claim 6 wherein said U-shaped open area is closed off at the upper end thereof by an arcuate slotted portion aligned with said main blade portion of said upper blade member.

8. The instrument of claim 1 wherein said handle portion of said upper blade member has a thumb rest formed in the lower end thereof.

9. The instrument of claim 1 wherein a port is provided on said upper blade member having a sealed chamber open at both the front and the rear of said upper blade member extending along one of said sidewalls of said upper blade member for receiving a suction tube therein.

10. The instrument of claim 1 wherein a port is provided on said upper blade member having a sealed chamber having an opening leading therein rearwardly of said upper blade member, said port extending along one of the sidewalls of said upper blade member.

11. The instrument of claim 10 including a portable light cone having a first tubular end receivable in said opening leading into said port, and an illuminating chamber coupled thereto for receiving a light source therein to emit light through said cone into said port.

12. The instrument of claim 11 wherein said illuminating chamber has a lens at the intersection of said cone and said chamber.

13. The instrument of claim 11 wherein said illuminating chamber has elongated tracks therein for guiding a light source inserted therein.

14. The instrument of claim 11 wherein the tip of said cone is tapered for insertion into said port.

15. The instrument of claim 11 wherein said chamber has an opening therethrough for expelling heat out of said chamber.

16. The instrument of claim 11 including a resilient sleeve mounted on said chamber rearwardly of said cone for accommodating light sources of varying sizes.

17. The instrument of claim 1 wherein said surgical instrument is of a molded transparent plastic material.

18. The instrument of claim 1 wherein said ratchet means includes at least one nub on said lower blade member engaging a grooved portion on said upper blade member.

19. The instrument of claim 18 wherein said ratchet means further includes an extension portion extending from said handle portion of said upper blade member through a slot in the handle portion of said lower blade member, said extension portion having a plurality of spaced ribs thereon engaging a second grooved portion on the handle portion of said first upper blade member.

* * * * *